United States Statutory Invention Registration [19]

[11] Reg. Number: H181

Koppes et al. [43] Published: Dec. 2, 1986

[54] BIS(2-FLUORO-2,2-DINITROETHOXY)ACETONITRILE AND A METHOD OF PREPARATION

[75] Inventors: William M. Koppes, Adelphi; Horst G. Adolph, Silver Spring, both of Md.

[73] Assignee: The United States of America as represented by the Secretary of the Navy, Washington, D.C.

[21] Appl. No.: 878,149

[22] Filed: Jun. 23, 1986

[51] Int. Cl.[4] ..... C06B 25/00

[52] U.S. Cl. ..... 149/88; 558/448; 149/19.1; 149/19.3

*Primary Examiner*—Edward A. Miller
*Assistant Examiner*—Susan Wolffe
*Attorney, Agent, or Firm*—Kenneth E. Walden; Roger D. Johnson

[57] ABSTRACT

Bis(2-fluoro-2,2-dinitroethoxy)acetonitrile, $N{\equiv}C{-}CH[OCH_2CF(NO_2)_2]_2$, is useful as a coplasticizer with bis(2-fluoro-2,2-dinitroethyl)formal in energetic plasticizer mixtures for plastic bonded explosives.

7 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BIS(2-FLUORO-2,2-DINITROETHOXY)ACETONITRILE AND A METHOD OF PREPARATION

BACKGROUND OF THE INVENTION

This invention relates to plastic-bonded explosives and more particularly to energetic plasticizers for plastic-bonded explosives.

Examples of energetic plasticizers which are currently used in plastic-bonded explosives (PBXs) are bis(2-fluoro-2,2-dinitroethyl)formal (FEFO), butanetriol trinitrate (BTTN), and trimethylolethane trinitrate (TMETN). These compounds have various disadvantages which include limited thermal stability (BTTN, TMETN), high volatility (FEFO), toxicity (FEFO), and high melting point (FEFO).

SUMMARY OF THE INVENTION

Accordingly, an object of this invention is to provide a novel organic compound.

Another object of this invention is to provide a new energetic coplasticizer for plastic-bonded explosives.

A further object of this invention is to provide an energetic coplasticizer having good thermal stability.

Still another object of this invention is to provide new energetic plasticizer mixtures.

A still further object of this invention is to provide an energetic plasticizer mixture having the same high energy content as FEFO but a lower volatility than FEFO.

These and other objects of this invention are achieved by providing a new compound bis(2-fluoro-2,2-dinitroethoxy)acetonitrile and a method of preparing it.

DETAILED DESCRIPTION OF THE PREFERRED EMBODIMENT

This invention provides bis(2-fluoro-2,2-dinitroethoxy)acetonitrile (CYANO-FEFO), $N{\equiv}C\text{-}CH[OCH_2CF(NO_2)_2]_2$, a new composition of matter, which has been found to act as a coplasticizer for bis(2-fluoro-2,2-dinitroethyl)formal (FEFO) in combination with various energetic and non-energetic prepolymers commonly used in plastic-bonded explosive (PBX) formulations. Bis(2-fluoro-2,2-dinitroethoxy)acetonitrile is a low melting solid (MP 41°−2° C.) with a liquid density at 23° C. of 1.62 g/cm$^3$. Its heat of formation is estimated to be −175 Kcal/mol, and the calculated detonation pressure is 244 Kbar.

The use of bis(2-fluoro-2,2-dinitroethoxy)acetonitrile (CYANO-FEFO) as a coplasticizer for bis(2-fluoro-2,2-dinitroethyl)formal (FEFO) provides several advantages over the use of FEFO as a unitary plasticizer. CYANO-FEFO is equal to FEFO in energy content (detonation pressure). Therefore, its addition to FEFO does not change the energy content of the system. CYANO-FEFO is miscible with FEFO in all proportions, and forms a binary eutectic of the approximate composition, FEFO:CYANO-FEFO=65:35, MP 5° C. Thus, the addition of this amount of CYANO-FEFO results in a significant decrease of the plasticizer melting point; this will convey improved lowtemperature properties to plastic-bonded explosives (PBXs) using the plasticizer mixture in place of neat FEFO. The volatility of CYANO-FEFO was determined by thermogravimetric analysis (TGA) at 117° C. The weight loss was 0.003 mg/min, compared to 0.039 mg/min for FEFO. Thus, the volatility of CYANO-FEFO is lower than that of FEFO by a factor of ten. The volatility of the plasticizer mixture will therefore be substantially lower than that of neat FEFO, and the volatility of FEFO will be reduced because of its reduced concentration.

The weight ratio of bis(2-fluoro-2,2-dinitroethyl)formal (FEFO) to bis(2-fluoro-2,2-dinitroethoxy)acetonitrile (CYANO-FEFO) in the energetic plasticizer mixture is preferably from 1:1 to 4:1, more preferably from 3:2 to 4:1 and most preferably about 13:7. Note that other energetic plasticizers may also be used in the plasticizer mixture. For example bis(2-fluoro-2,2-dinitroethyl)amine (BFDNA) works well with CYANO-FEFO as a coplasticizer.

Bis(2-fluoro-2,2-dinitroethoxy)acetonitrile can be prepared from 2-fluoro-2,2-dinitroethanol by the following reaction sequence as described in examples 1, 2, and 3:

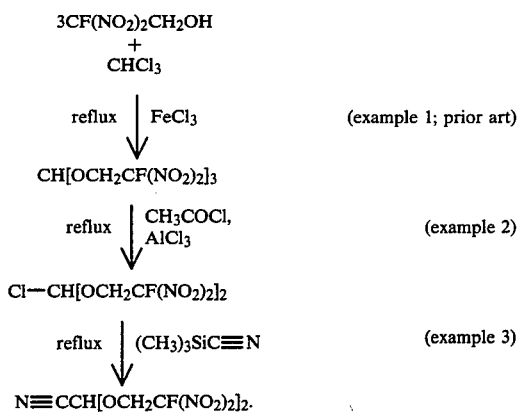

Tris(2-fluoro-2,2-dinitroethoxy)methane, $CH[OCH_2CF(NO_2)_2]_3$, is a prior art compound which is synthesized by reacting three moles of 2-fluoro-2,2-dinitroethanol with one mole of chloroform by refluxing the reactants in the presence of ferric chloride as a catalyst. The conditions of this reaction are illustrated by example 1 which is incorporated from U.S. Pat. No. 3,388,147, entitled "2-Fluoro-2,2-Dinitroethyl Carbonates and Production thereof," which was issued on June 11, 1968, to Mortimer J. Kamlet et al. (see col. 3, example III).

Next, the tris(2-fluoro-2,2-dinitroethoxy)methane is refluxed with aluminum chloride and acetyl chloride to produce chloro bis(2-fluoro-2,2-dinitroethoxy)methane as illustrated by example 2.

Finally, one mole of cyanotrimethylsilane is reacted with each mole of chloro bis(2-fluoro-2,2-dinitroethoxy)methane to produce the desired product, bis(2-fluoro-2,2-dinitroethoxy)acetonitrile, under conditions illustrated by example 3. The choice of a solvent for this step is not critical. Any inert solvent in which the reactants are soluble and which has a suitable boiling point may be used. Suitable solvents include dichloromethane, 1,1-dichloroethane, 1,2-dichloroethane, 1,1,2-trichloroethane, or mixtures thereof.

The general nature of the invention having been set forth, the following examples are presented as specific examples thereof. It will be understood that the invention is not limited to these specific examples but is susceptible to various modifications that will be recognized by one of ordinary skill in the art.

EXAMPLE 1

(Prior Art)

Tris(2-fluoro-2,2-dinitroethoxy)methane [i.e., tris(2-fluoro-2,2-dinitroethyl)orthoformate]

"A mixture of 0.5 g. anhydrous ferric chloride and 10 ml. chloroform was placed in a 30 ml. round-bottom flask fitted with a magnetic stirrer and a reflux condenser connected through a bubbler to a methanol gas trap. 2-fluoro-2,2-dinitroethanol, 2.0 g. (0.013 mole) was added and the mixture stirred and refluxed for 24 hours, after which time the mixture was collected [sic] to room temperature and the solvent removed in vacuo.

The residue was drowned in iced water, stirred until the ferric chloride dissolved and the crystalline product collected. Recrystallization of this material from chloroform-hexane gave 1.39 g. (68%) pure tris(2-fluoro-2,2-dinitroethyl)orthoformate (FDNEOF) as fine colorless needles, M.P. 110°-111.2°."

EXAMPLE 2

Chloro bis(2-fluoro-2,2-dinitroethoxy)methane

A solution of tris(2-fluoro-2,2-dinitroethoxy)methane (23.6 g, 0.050 mol), aluminum chloride (12.0 g, 0.090 mol) and acetyl chloride (200 g) was refluxed for 1.5 hours and then concentrated on a rotary evaporator to a viscous liquid. This was extracted with chloroform (2×50 ml). After treatment with activated charcoal (2 g), this solution was filtered and concentrated (rot. evap., 40° C. bath) to 23 g of residue from which 8.53 g (87%) of 2-fluoro-2,2-dinitroethyl acetate (bp 40°−3° C./0.1 mm) was removed by distillation. The residual liquid (14.14 g, 80% yield) was chloro bis(2-fluoro-2,2-dinitroethoxy)methane, free of contaminants by $^1H$ NMR analysis.

Anal. Calcd for $C_5H_5ClF_2N_4O_{10}$: C, 16.94; H, 1.42; Cl, 10.00; F, 10.72; N, 15.80. Found: C, 17.10; H, 1.78; Cl, 10.08; F, 10.71; N, 15.42.

EXAMPLE 3

Cyano bis(2-fluoro-2,2-dinitroethoxy)methane (or bis(2-fluoro-2,2-dinitroethoxy)acetonitrile)

A solution of chloro bis(2-fluoro-2,2-dinitroethoxy)methane (2.45, 6.9 mmol) prepared in example 2 and cyanotrimethylsilane (0.77 g, 7.8 mmol) in 15 ml of dichloroethane was refluxed for 40 hours. NMR analysis showed consumption of the chloroformal and the presence of the cyanoformal together with a small amount of 2-fluoro-2,2-dinitroethyl formate. A 2.45 g residue from concentration of the reaction solution on a rotary evaporator was chromatographed on Silica Gel 60 (70-230 mesh, 25 g) with a 3:2 solvent mixture of hexanes/dichloromethane to give 1.51 g (63%) of bis(2-fluoro-2,2-dinitroethoxy)acetonitrile: mp 41°−2°; IR (film) 2260 (CN, weak) $cm^{-1}$; $^1H$ NMR ($CDCl_3$): δ5.67 (s,l), 4.87 (d, 4, J=16 Hz); mass spectrum (CI, $CH_4$), m/z (rel intensity): 386 (M+41, 3), 375 (M+30, 2), 319 (100), 92 (50).

Anal. Calcd for $C_6H_5F_2N_5O_{10}$: C, 20.88; H, 1.46; F, 11.01; N, 20.29. Found: C, 21.05; H, 1.62; F, 10.87; N, 20.38.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed as new and desirable to be secured by Letters Patent of the United States is:

1. Bis(2-fluoro-2,2-dinitroethoxy)acetonitrile, $$N{\equiv}CCH[OCH_2CF(NO_2)_2]_2.$$

2. An energetic plasticizer comprising a mixture of bis(2-fluoro-2,2-dinitroethyl)formal and bis(2-fluoro-2,2-dinitroethoxy)acetonitrile.

3. An energetic plasticizer according to claim 2 wherein the weight ratio of bis(2-fluoro-2,2-dinitroethyl)formal to bis(2-fluoro-2,2-dinitroethoxy)acetonitrile is from 1:1 to 4:1.

4. An energetic plasticizer according to claim 3 wherein the weight ratio of bis(2-fluro-2,2-dinitroethyl)formal to bis(2-fluoro-2,2-dinitroethoxy)acetonitrile is from 3:2 to 4:1.

5. An energetic plasticizer according to claim 4 wherein the weight ratio of bis(2-fluoro-2,2-dinitroethyl)formal to bis(2-fluoro-2,2-dinitroethoxy)acetonitrile is about 13:7.

6. A method of preparing bis(2-fluoro-2,2-dinitroethoxy)acetonitrile comprising the following steps in order:

(1) refluxing tris(2-fluoro-2,2-dinitroethoxy)methane with aluminum chloride and acetyl chloride to produce chloro bis(2-fluoro-2,2-dinitroethoxy)methane;

(2) reacting one mole of cyanotrimethylsilane with one mole of chloro bis(2-fluoro-2,2-dinitroethoxy)methane to produce bis(2-fluoro-2,2-dinitroethoxy)acetonitrile; and (3) isolating the product bis(2-fluoro-2,2-dinitroethoxy)acetonitrile.

7. The process of claim 6 wherein the reaction in step (2) is run under reflux in a solvent selected from the group consisting of dichloromethane, 1,1-dichloroethane, 1,2-dichloroethane, 1,1,2-trichloroethane, and mixtures thereof.

* * * * *